(12) United States Patent
Nakamura et al.

(10) Patent No.: US 10,756,574 B2
(45) Date of Patent: Aug. 25, 2020

(54) MEDICAL TOOL

(71) Applicant: Sony Olympus Medical Solutions Inc., Tokyo (JP)

(72) Inventors: Takuya Nakamura, Tokyo (JP); Toshiya Sugai, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 416 days.

(21) Appl. No.: 15/632,893

(22) Filed: Jun. 26, 2017

(65) Prior Publication Data

US 2018/0008304 A1  Jan. 11, 2018

(30) Foreign Application Priority Data

Jul. 6, 2016 (JP) .................................. 2016-134516

(51) Int. Cl.
*H02J 50/10* (2016.01)
*A61B 17/32* (2006.01)
(Continued)

(52) U.S. Cl.
CPC .......... *H02J 50/10* (2016.02); *A61B 1/00029* (2013.01); *A61B 1/00032* (2013.01); *A61B 1/00055* (2013.01); *A61B 17/320092* (2013.01); *G02B 23/2407* (2013.01); *G02B 23/2484* (2013.01); *H02J 7/025* (2013.01); *A61B 1/00066* (2013.01); *A61B 1/042* (2013.01); *A61B 2017/00734* (2013.01); *G02B 23/2469* (2013.01); *H02J 1/10* (2013.01); *H02J 7/0047* (2013.01); *H02J 7/0068* (2013.01); *H02J 7/345* (2013.01); *H04N 2005/2255* (2013.01)

(58) Field of Classification Search
CPC ............ A61B 1/00029; A61B 1/00032; A61B 1/0005; A61B 1/00105; A61B 2018/1226; A61B 18/2023; G02B 23/2407
See application file for complete search history.

(56) References Cited

U.S. PATENT DOCUMENTS 3,812,505 A * 5/1974 Elliott ...................... A61B 1/04
396/21
4,924,852 A * 5/1990 Suzuki ................. A61B 1/0052
600/107
(Continued)

FOREIGN PATENT DOCUMENTS

JP  2000-287987 A  10/2000
JP  2005-152209 A  6/2005
(Continued)

OTHER PUBLICATIONS

Japanese Office Action dated Jun. 23, 2020, in corresponding Japanese Patent Application No. 2016-134516.

*Primary Examiner* — Timothy J Neal
*Assistant Examiner* — Jae Woo
(74) *Attorney, Agent, or Firm* — Xsensus LLP (57) ABSTRACT

A medical tool includes: a tool main unit configured to be driven in response to a power supply; a first power supply configured to be removable from the tool main unit; and a second power supply having a smaller power capacity than the first power supply, and configured to be charged by the first power supply. The tool main unit is configured to be driven by receiving power supply from one of the first power supply and the second power supply.

10 Claims, 8 Drawing Sheets

(51) Int. Cl.
   A61B 1/00 (2006.01)
   G02B 23/24 (2006.01)
   H02J 7/02 (2016.01)
   A61B 1/04 (2006.01)
   H02J 7/00 (2006.01)
   H02J 7/34 (2006.01)
   H02J 1/10 (2006.01)
   A61B 17/00 (2006.01)
   H04N 5/225 (2006.01)

(56) References Cited

U.S. PATENT DOCUMENTS

| | | | | |
|---|---|---|---|---|
| 5,357,187 A * | 10/1994 | Park | ............ | H01M 10/44 320/116 |
| 5,666,006 A * | 9/1997 | Townsley | ............ | H02J 7/0024 307/43 |
| 6,099,465 A * | 8/2000 | Inoue | ............ | A61B 1/05 348/75 |
| 6,133,711 A * | 10/2000 | Hayashi | ............ | G01R 31/3648 320/106 |
| 6,494,827 B1 * | 12/2002 | Matsumoto | ............ | A61B 1/00032 600/117 |
| 6,920,575 B2 * | 7/2005 | Odaohhara | ............ | G06F 1/30 713/300 |
| 7,139,016 B2 * | 11/2006 | Squilla | ............ | A61B 1/00048 348/66 |
| 7,422,559 B2 * | 9/2008 | Kehoskie | ............ | G02B 23/2492 348/82 |
| 2004/0001333 A1 * | 1/2004 | Gentz | ............ | A61B 1/00096 362/103 |
| 2005/0004474 A1 * | 1/2005 | Iddan | ............ | A61B 1/00158 600/476 |
| 2005/0129108 A1 * | 6/2005 | Bendall | ............ | A61B 1/00039 375/240.01 |
| 2005/0154294 A1 * | 7/2005 | Uchiyama | ............ | A61B 1/00029 600/420 |
| 2005/0189923 A1 * | 9/2005 | Ohishi | ............ | G03G 15/0283 320/138 |
| 2005/0251017 A1 * | 11/2005 | Azar | ............ | A61B 1/00158 600/407 |
| 2006/0199146 A1 * | 9/2006 | Mandelkern | ............ | A61B 1/00016 433/52 |
| 2006/0293565 A1 * | 12/2006 | Uchimura | ............ | A61B 1/00016 600/156 |
| 2008/0150754 A1 * | 6/2008 | Quendt | ............ | A61B 1/00016 340/870.07 |
| 2009/0058361 A1 * | 3/2009 | John | ............ | A61N 1/3785 320/128 |
| 2010/0030020 A1 * | 2/2010 | Sanders | ............ | A61B 1/00105 600/109 |
| 2011/0018988 A1 * | 1/2011 | Kazakevich | ............ | A61B 1/00016 348/68 |
| 2011/0115891 A1 * | 5/2011 | Trusty | ............ | A61B 1/00016 348/65 |

FOREIGN PATENT DOCUMENTS

| | | |
|---|---|---|
| JP | 2006-115909 A | 5/2006 |
| JP | 2008-29480 A | 2/2008 |
| JP | 2009-95554 A | 5/2009 |
| JP | 2009-213878 A | 9/2009 |
| JP | 2015-131120 | 7/2015 |
| JP | 2015-231551 | 12/2015 |
| WO | 2016/071992 A1 | 5/2016 |

* cited by examiner

MEDICAL TOOL

CROSS-REFERENCE TO RELATED APPLICATION(S)

The present application claims priority to and incorporates by reference the entire contents of Japanese Patent Application No. 2016-134516 filed in Japan on Jul. 6, 2016.

BACKGROUND

The present disclosure relates to a medical tool.

Various types of medical tools have been known in the medical field (see Japanese Patent Application Laid-open No. 2015-131120 and Japanese Patent Application Laid-open No. 2015-231551, for example).

The medical tool disclosed in Japanese Patent Application Laid-open No. 2015-131120 is an endoscope camera (hand-held type unit) for capturing images of interior of a subject such as a person (interior of a living body). This endoscope camera includes an endoscope having an insertion tube to be inserted into the interior of the living body, an LED end coupler that supplies light for illuminating the interior of the living body to the insertion tube, and an imaging unit that generates image signals by picking up images of the subject via the insertion tube and the LED end coupler, and wirelessly transmits the image signals to an external camera control unit. These three units are removably provided. In other words, the endoscope camera and the external camera control unit are wirelessly connected without any cable. The external camera control unit then processes the image signals having been received wirelessly from the endoscope camera (imaging unit), and displays a captured image that is based on the image signals on a display unit. The endoscope camera also includes a first battery module dedicated to the LED end coupler, and a second battery module dedicated to the imaging unit so that the electrical contact between the LED end coupler and the imaging unit may be omitted.

The medical tool disclosed in Japanese Patent Application Laid-open No. 2015-231551 is an energy treatment tool (hand-held ultrasound surgery cautery cutting device) that treats biological tissues by applying ultrasonic energy to the biological tissues. This energy treatment tool includes a treating unit (an ultrasound cutting blade and a waveguide assembly that applies ultrasonic energy), a control unit (TAG assembly) that generates ultrasonic energy (ultrasonic vibration) for the treating unit, and a power supply unit (battery assembly) that supplies power to the control unit, and these three units are removably provided.

SUMMARY

However, in the endoscope camera disclosed in Japanese Patent Application Laid-open No. 2015-131120, the first battery module and the second battery module respectively serve as battery modules dedicated to the LED end coupler and the imaging unit. Therefore, when the charge remaining in the first battery module (the charge remaining in the power supply) is low, driving of the LED end coupler fails, and when the charge remaining in the second battery module is low, driving of the imaging unit fails. In other words, when the charge remaining in one of the first and the second battery modules becomes low, the captured image being displayed suddenly disappears (hereinafter, referred to as image disappearance), so that the endoscope camera becomes inoperable.

In the same manner, in the energy treatment tool disclosed in Japanese Patent Application Laid-open No. 2015-231551, when the charge remaining in the power supply unit becomes low, the energy treatment tool becomes incapable of generating ultrasonic energy for the treating unit, and becomes inoperable.

There is a need for a medical tool that does not become inoperable even if charge remaining in a power supply unit becomes low.

A medical tool according to one aspect of the present disclosure may include: a tool main unit configured to be driven in response to a power supply; a first power supply configured to be removable from the tool main unit; and a second power supply having a smaller power capacity than the first power supply, and configured to be charged by the first power supply. The tool main unit is configured to be driven by receiving power supply from one of the first power supply and the second power supply.

DETAILED DESCRIPTION

Some embodiments for implementing the present disclosure (hereinafter, referred to as embodiments) will now be explained with reference to some drawings. The embodiments explained below are not intended to limit the scope of the present disclosure in any way. Furthermore, in the drawings, the same parts are assigned with the same reference numerals.

First Embodiment

General Configuration of Endoscope Camera System

Figure 1:
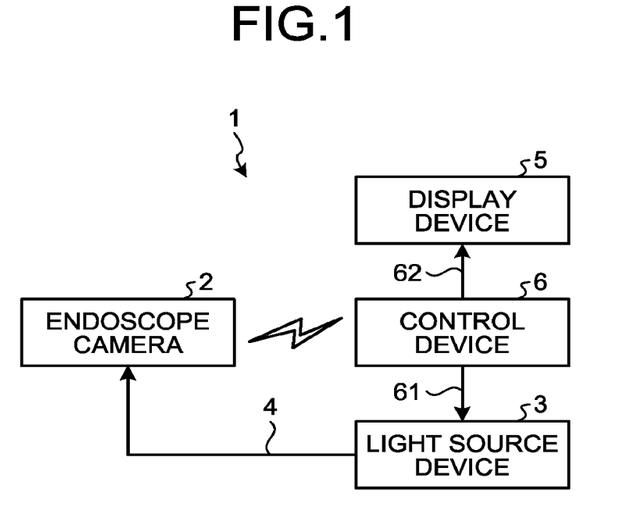
FIG. 1 is a schematic illustrating a general configuration of an endoscope camera system according to a first embodiment of the present disclosure.

FIG. 1 is a schematic illustrating a general configuration of endoscope camera system 1 according to a first embodiment of the present disclosure.

The endoscope camera system 1 is used in the medical field, and is a system for observing the interior of a subject such as a person (the interior of a living body). The endoscope camera system 1 includes an endoscope camera 2, a light source device 3, a light guide cable 4, a display device 5, and a control device 6, as illustrated in FIG. 1.

The endoscope camera 2 corresponds to a medical tool according to the present disclosure. The endoscope camera 2 includes an inserted portion 21 (see FIG. 2) that is to be inserted into the interior of the living body, that captures images of the interior of the living body while illuminating the interior of the living body with the light supplied by the light source device 3 from the tip of the inserted portion 21, and that generates image signals. The endoscope camera 2 connects to communicate with the control device 6 over a predetermined communication protocol, and transmits the generated image signals wirelessly to the control device 6.

More specific configurations of the endoscope camera 2 will be described later.

The light source device 3 is connected to one end of the light guide cable 4 (FIG. 1), and supplies the light for illuminating the interior of the living body to the one end of the light guide cable 4, under the control of the control device 6.

One end of the light guide cable 4 is removably connected to the light source device 3, and the other end is removably connected to the inserted portion 21. The light guide cable 4 then communicates the light supplied by the light source device 3 from the one end of the light guide cable 4 to the other end, to supply the light to the inserted portion 21.

The display device 5 is provided using a display such as a liquid crystal display or an organic electro-luminescence (EL) display, and displays a captured image that is based on video signals processed by the control device 6.

The control device 6 corresponds to the external device according to the present disclosure. The control device 6 includes a central processing unit (CPU) or the like, and connects to communicate with the endoscope camera 2 over a predetermined communication protocol, and is connected to the light source device 3 and the display device 5 via a first transfer cable 61 and a second transfer cable 62, respectively. The control device 6 applies various types of image processing to the image signals received from the endoscope camera 2, and generates video signals to be displayed, and outputs the video signals to the display device 5 via the second transfer cable 62. The control device 6 also transmits control signals and the like wirelessly to the endoscope camera 2, and outputs control signals to the light source device 3 via the first transfer cable 61.

Configuration of Endoscope Camera

Figure 2:
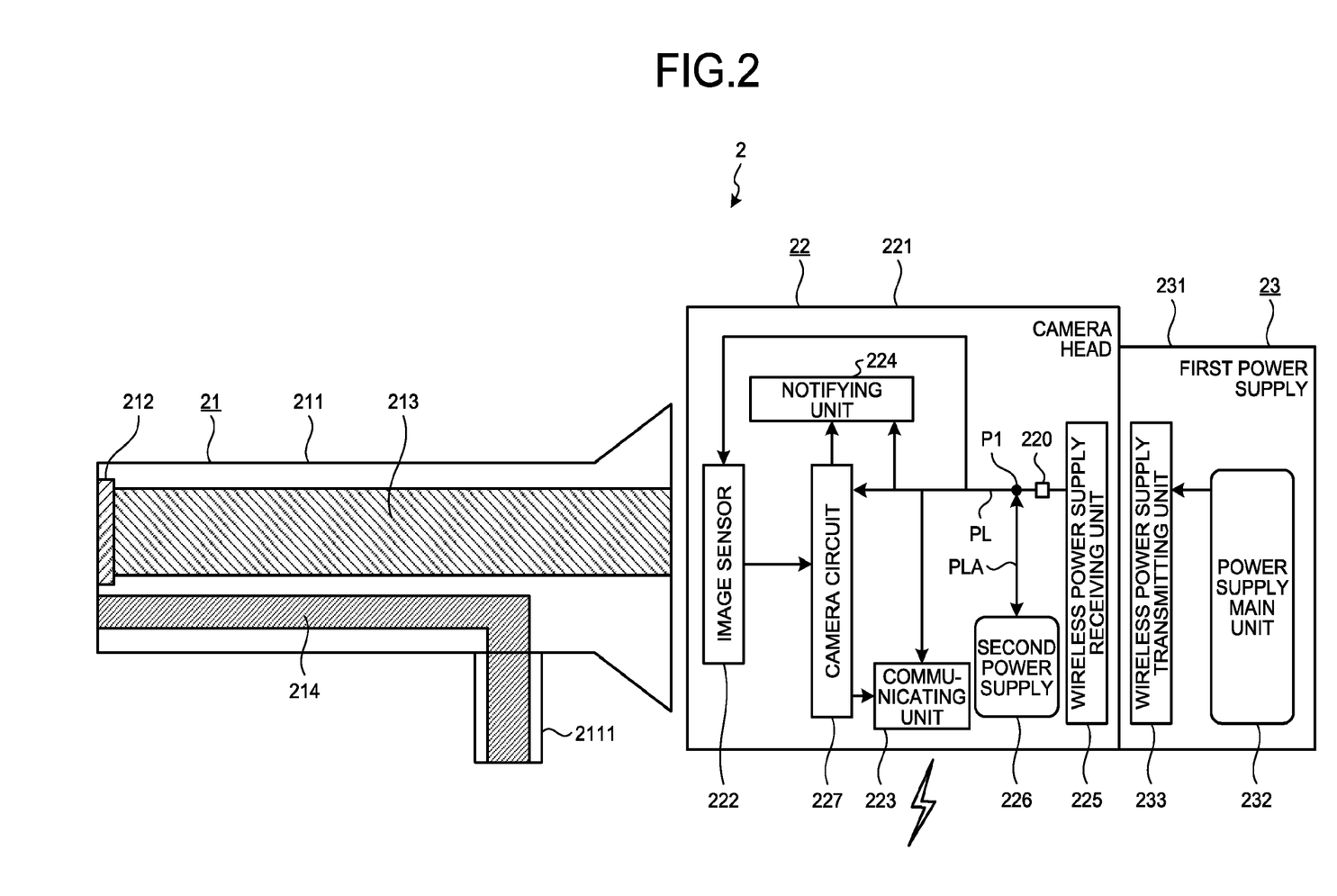
FIG. 2 is a schematic illustrating a configuration of the endoscope camera illustrated in FIG. 1.

FIG. 2 is a schematic illustrating a configuration of the endoscope camera 2.

The endoscope camera 2 includes the inserted portion 21, a camera head 22, and a first power supply 23, as illustrated in FIG. 2.

The inserted portion 21 is a part that is inserted into the interior of the living body, and includes an insertion tube 211, an object lens 212, a relay lens 213, and a light guide 214.

The insertion tube 211 is hard or at least partly soft, and has a thin and long shape. Provided to the external circumferential surface of the insertion tube 211 is a connection connector 2111 protruding in the radial direction, and connected with the other end of the light guide cable 4.

The object lens 212 is provided internal of the tip of the inserted tube 211, and collects the light of the image of the subject.

The relay lens 213 is provided internal of the insertion tube 211, and guides the image of the subject collected by the object lens 212 to the base end of the insertion tube 211.

The light guide 214 is laid from the tip of the internal of the insertion tube 211 to the base end thereof, and extends in a manner bending toward the connection connector 2111 substantially at a right angle. With the light guide cable 4 connected to the connection connector 2111, the tip of the inserted portion 21 outputs the light supplied by the light source device 3 via the light guide cable 4 and the light guide 214, and the light is emitted toward the interior of the living body.

The camera head 22 has a function as the tool main unit according to the present disclosure, and is removably connected to the base end of the inserted portion 21. The camera head 22 includes a sealed enclosure 221, an image sensor 222, a communicating unit 223, a notifying unit 224, a wireless power supply receiving unit 225, a second power supply 226, and a camera circuit 227, as illustrated in FIG. 2.

The sealed enclosure 221 has a shape of a container a part of which has an opening (not illustrated), and the members 222 to 227 are housed inside of the sealed enclosure 221.

On the side surface of the sealed enclosure 221 provided with the opening, a coupler unit (not illustrated) to be removably connected with the base end of the inserted portion 21 is provided. The opening is sealed with a translucent member (not illustrated) such as glass allowing the image of the subject collected by the inserted portion 21 to be transmitted. Therefore, the internal of the sealed enclosure 221 is kept sealed. On the external surface of the sealed enclosure 221, a connecting unit (not illustrated) to be mechanically connected (to be connected electrically contactlessly) to the first power supply 23 is provided.

The image sensor 222 has a function as the imaging unit according to the present disclosure, and is driven by receiving the power supply from the first power supply 23 or the second power supply 226 via a power supply line PL (FIG. 2), and picks up the images of the interior of the living body under the control of the camera circuit 227. The image sensor 222 is implemented using a sensor chip in which an image sensor (not illustrated), such as a charge coupled device (CCD) or a complementary metal oxide semiconductor (CMOS), is integrated with a signal processing unit (not illustrated). In the image sensor 222, the image sensor receives the image of the subject collected by the inserted portion 21, and converts the image into an electric signal, and the signal processing for applies signal processing (such as A/D conversion) to the electric signals (analog signals) received form the image sensor, and outputs the image signals. Subsequently to the A/D conversion, the image sensor 222 outputs the image signal (digital signal). The signal processing unit (not illustrated) may be provided as a separate unit, without being integrated with the image sensor.

The communicating unit 223 is a communication interface that is driven by receiving the power supply from the first power supply 23 or the second power supply 226 via the power supply line PL under the control of the camera circuit 227, and communicates various data including signals used for the wireless communication with the control device 6.

Used in the first embodiment as a wireless communication protocol is Wireless Fidelity (Wi-Fi) (registered trademark) in a frequency band of 2.4 GHZ, 5 GHZ, or 60 GHZ. As the wireless communication protocol, any known communication protocols other than Wi-Fi (registered trademark) may also be used.

The notifying unit 224 is driven by receiving the power supply from the first power supply 23 or the second power supply 226 via the power supply line PL, and notifies predetermined information under the control of the camera circuit 227. Examples of the notifying unit 224 include a light emitting diode (LED) notifying the predetermined information by turning on or blinking, and a display device displaying the predetermined information, and a speaker outputting the predetermined information as sound.

The wireless power supply receiving unit 225 is a power receiver used for wirelessly supplying power in accordance with Qi or PMA, for example, and is connected contactlessly with the first power supply 23 while the first power supply 23 is connected to the connecting unit (not illustrated) of the sealed enclosure 221, and wirelessly supplies the power supplied by the first power supply 23 to the power supply line PL.

The second power supply 226 is connected to the power supply line PL via an auxiliary power supply line PLA (FIG. 2), and supplies power to the image sensor 222, the communicating unit 223, the notifying unit 224, and the camera circuit 227 via the auxiliary power supply line PLA and the power supply line PL so that the camera head 22 (the members 222, 223, 224, 227) may be driven by the power. A backflow prevention circuit 220 (FIG. 2) for preventing the backflow of current from the second power supply 226 toward the side of the wireless power supply receiving unit 225 is provided between a connecting position P1 at which the power supply line PL is connected to the auxiliary power supply line PLA (FIG. 2), and the wireless power supply receiving unit 225.

When the charge remaining in the second power supply 226 is low, the second power supply 226 is charged wirelessly by the first power supply 23, with the power supplied to the power supply line PL from the wireless power supply receiving unit 225.

Figure 4:
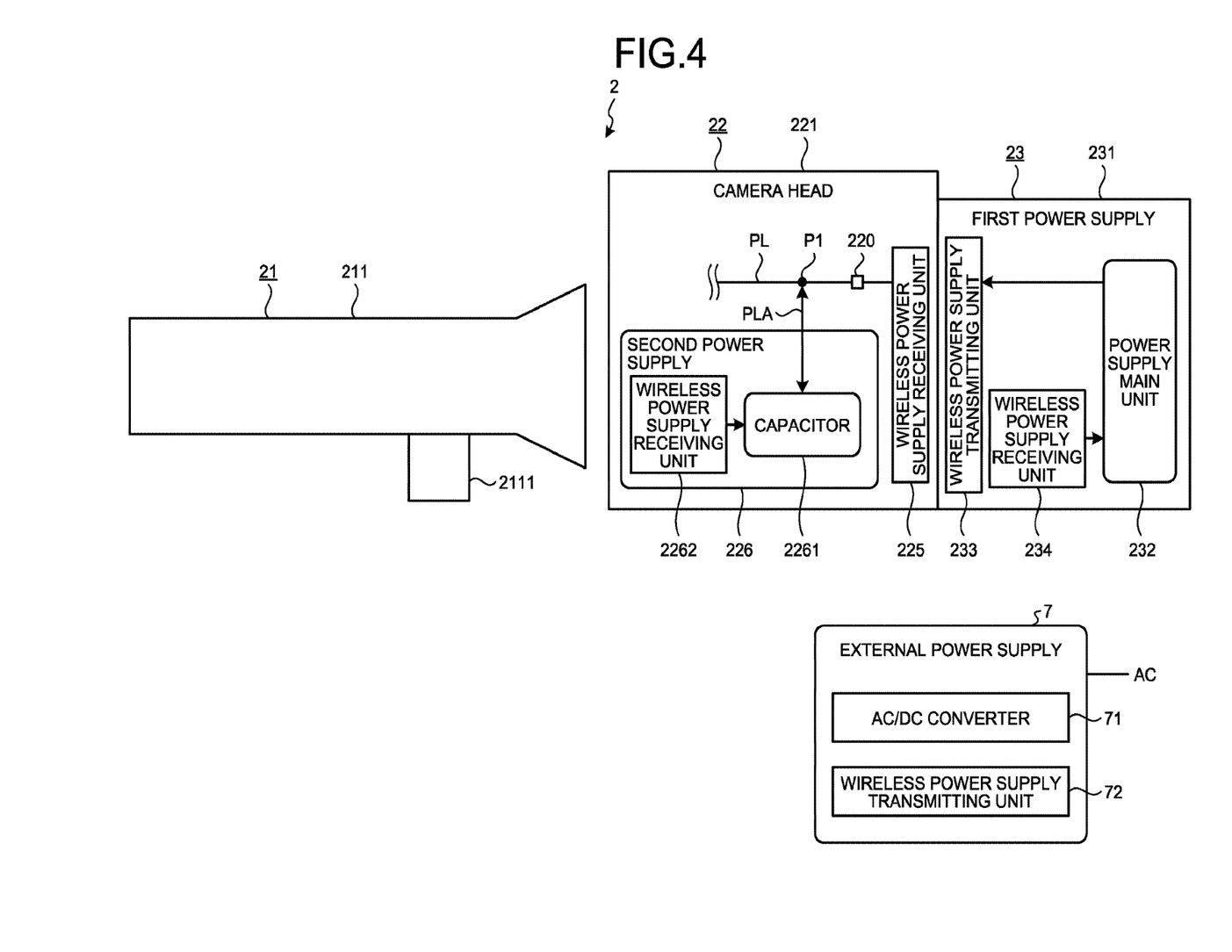
FIG. 4 is a schematic illustrating an example of a way in which the first power supply and the second power supply are charged before the use of the endoscope camera illustrated in FIG. 2.

In the first embodiment, the second power supply 226 has a smaller power capacity than the first power supply 23 does, and is charged by the first power supply 23, and includes a capacitor 2261 for supplying power to the members 222, 223, 224, 227 (see FIG. 4). In the explanation hereunder, for the convenience of explanations, the power capacity of the first power supply 23 will be referred to as a first power capacity, and the power capacity of the second power supply 226 will be referred so as a second power capacity.

The camera circuit 227 includes a CPU or the like, and is driven by receiving the supply of power from the first power supply 23 or the second power supply 226 via the power supply line PL to control the entire camera head 22. Specifically, the camera circuit 227 establishes a communication connection with the control device 6 over a communication protocol such as Wi-Fi (registered trademark), via the communicating unit 223. The camera circuit 227 causes the image sensor 222 to pick up the image based on the control signal received from the control device 6 via the communicating unit 223, processes the generated image signals, and transmits the image signals wirelessly to the control device 6 via the communicating unit 223. The camera circuit 227 also has a monitoring function for monitoring the charge remaining in the first power supply 23 and the second power supply 226, and causes the notifying unit 224 to notify the monitoring results.

The function of the camera circuit 227 for monitoring the charge remaining in the power supply will be explained more in detail, following the explanation of the configuration of the first power supply 23.

As explained above, the camera head 22 receives the power supplied by the first power supply 23, and transmits and receives image signals and the like to and from the control device 6 wirelessly, and the sealed enclosure 221 (including the coupler unit and the translucent members) keeps the internal of the camera head 22 sealed. In this manner, it is possible to prevent any liquid from infiltrating into the internal of the camera head 22 during the disinfection or sterilization, for example, and to prevent the members provided internal to the camera head 22, such as the camera circuit 227, from being damaged by the liquid, or to prevent any image from being deteriorated due to the liquid being attached to the image sensor 222, for example.

The first power supply 23 includes, as illustrated in FIG. 2, a sterilized enclosure 231, a power supply main unit 232, and a wireless power supply transmitting unit 233.

The sterilized enclosure 231 is an enclosure sterilized in advance, and the members 232, 233 are housed in the internal of the sterilized enclosure 231 in such a manner that the entire members 232, 233 are covered thereby.

Provided on the external surface of the sterilized enclosure 231 is a connecting unit (not illustrated) to be mechanically connected (to be connected electrically contactlessly) to the sealed enclosure 221. In other words, the first power supply 23 is provided removably from the camera head 22, because the connecting units are provided to the sealed enclosure 221 and the sterilized enclosure 231.

The power supply main unit 232 is provided as a secondary battery, and is electrically connected to the wireless power supply transmitting unit 233 while the power supply main unit 232 is mounted inside of the sterilized enclosure 231, and supplies the power for driving the camera head 22 to the wireless power supply transmitting unit 233.

The wireless power supply transmitting unit 233 is used for wireless power supply such as that in accordance with Qi or PMA, and is a power transmitter compatible with the wireless power supply receiving unit 225, and is fixed internal of the sterilized enclosure 231. The wireless power supply transmitting unit 233 connects contactlessly with the camera head 22 (wireless power supply receiving unit 225), and supplies the power wirelessly to the camera head 22, with the first power supply 23 mounted on the camera head 22.

The power supply main unit 232 not having been sterilized is held in the sterilized enclosure 231. As the way in which the power supply main unit 232 is held in the sterilized enclosure 231, a way for mounting the power supply main unit 232 using a bag-like sheet capable of holding the power supply main unit 232 may be used, for example (see Japanese Patent Application Laid-open No. 2006-110192 (FIGS. 10 to 14)).

Function of Camera Circuit for Monitoring Remaining Charge in Power Supply

The function of the camera circuit 227 for monitoring the charge remaining in the power supply will now be explained.

Figure 3:
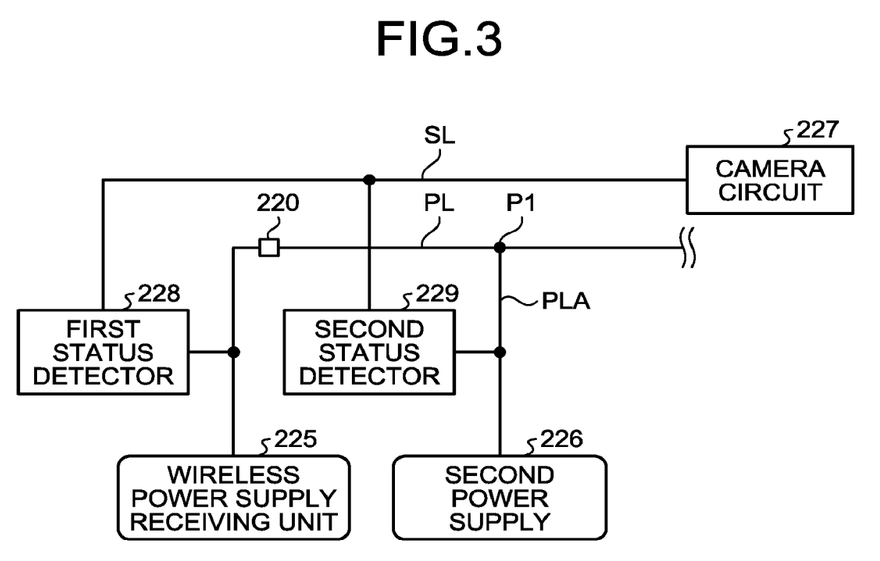
FIG. 3 is a schematic illustrating a function of the camera circuit monitoring the charge remaining in the power supply illustrated in FIG. 2.

FIG. 3 is a schematic illustrating the function of the camera circuit 227 for monitoring the charge remaining in the power supply.

The camera head 22 includes, as illustrated in FIG. 3, a first status detector 228 and a second status detector 229, in addition to the members 221 to 227 described above.

The first status detector 228 is a part that detects the status of the first power supply 23. Specifically, the first status detector 228 is connected between the connecting position P1 at which the power supply line PL is connected to the auxiliary power supply line PLA, and the wireless power supply receiving unit 225, and detects the electric potential at the connecting position (the remaining charge in the first power supply 23). The first status detector 228 then outputs the detection result to the camera circuit 227 via the signal line SL (FIG. 3).

The second status detector 229 is a part that detects the status of the second power supply 226. Specifically, the second status detector 229 connects to the auxiliary power supply line PLA, and detects the electric potential at the connecting position (the remaining charge in the second power supply 226). The second status detector 229 then outputs the detection result to the camera circuit 227 via the signal line SL.

The camera circuit 227 receives an input of the detection result of the first status detector 228 (the remaining charge in the first power supply 23), and constantly monitors whether the remaining charge in the first power supply 23 is lower than a first threshold. In this manner, the camera circuit 227 recognizes whether the remaining charge in the first power supply 23 is dropping below the level required for driving the camera head 22.

The camera circuit 227 also receives an input of the detection result from the second status detector 229 (the remaining charge in the second power supply 226), and constantly monitors whether the remaining charge in the second power supply 226 is lower than a second threshold. In this manner, the camera circuit 227 recognizes whether the remaining charge in the second power supply 226 is dropping below the level suitable for driving the camera head 22.

As a result of monitoring, if the camera circuit 227 recognizes that the remaining charge in the first power supply 23 or the second power supply 226 is dropping below the level suitable for driving the camera head 22, the camera circuit 227 causes the notifying unit 224 to notify the predetermined information by controlling the operation of the notifying unit 224.

Possible Usage of Endoscope Camera

A way in which the endoscope camera 2 is used during a surgical operation or the like will now be explained.

Before explaining the way in which the endoscope camera 2 is used, a way in which the first power supply 23 and the second power supply 226 are changed before the use of the endoscope camera 2 will now be explained.

FIG. 4 is a schematic illustrating an example of a way in which the first power supply 23 and the second power supply 226 are charged before the use of the endoscope camera 2.

In FIG. 4, for the convenience of explanation, the members 212 to 214 of the inserted portion 21 and the members 222 to 224, 227 of the camera head 22 are not illustrated.

Before the use of the endoscope camera 2, the first power supply 23 and the second power supply 226 are charged with the power supplied from an external power supply 7, as illustrated in FIG. 4.

The external power supply 7 includes an alternating-current-to-direct-current (AC/DC) converter 71, and a wireless power supply transmitting unit 72.

The AC/DC converter 71 converts the AC voltage from an AC power supply into DC voltage, and supplies the DC voltage to the wireless power supply transmitting unit 72.

The wireless power supply transmitting unit 72 is a power transmitter that is used for wireless power supply, in accordance with Qi or PMA, for example, and connects contactlessly with the first power supply 23 and the second power supply 226, and supplies the power to the first power supply 23 and to the second power supply 226.

The second power supply 226 includes, as illustrated in FIG. 4, a wireless power supply receiving unit 2262, in addition to the capacitor 2261 described above.

The wireless power supply receiving unit 2262 is used for wireless power supply in accordance with Qi or PMA, for example, and is a power receiver compatible with the wireless power supply transmitting unit 72. The wireless power supply receiving unit 2262 connects contactlessly with the wireless power supply transmitting unit 72, and supplies the power wirelessly supplied from the external power supply 7 to the capacitor 2261 to charge the capacitor 2261.

The first power supply 23 includes, as illustrated in FIG. 4, a wireless power supply receiving unit 234, in addition to the members 231 to 233 described above.

The wireless power supply receiving unit 234 is used in wireless power supply in accordance with Qi or PMA, for example, and is a power receiver compatible with the wireless power supply transmitting unit 72, and is fixed internal of the sterilized enclosure 231. The wireless power supply receiving unit 234 is electrically connected to the power supply main unit 232 with the power supply main unit 232 held in the sterilized enclosure 231. The wireless power supply receiving unit 234 connects contactlessly with the wireless power supply transmitting unit 72, and supplies the power wirelessly supplied from the external power supply 7 to the power supply main unit 232 to charge the power supply main unit 232.

With the configuration described above, the first power supply 23 and the second power supply 226 are charged with the power supplied by the external power supply 7 before the use of the endoscope camera 2.

A way in which the power is supplied to the camera head 22 from the first power supply 23 or the second power supply 226 during the use of the endoscope camera 2 will now be explained.

In other words, because the first power supply 23 and the second power supply 226 are charged in the manner described above, and the first power capacity is greater than the second power capacity (the electric potential at the connecting position P1 between the power supply line PL and the wireless power supply receiving unit 225 is higher than the electric potential at the auxiliary power supply line PLA), the camera head 22 is driven by the power supplied by the first power supply 23. At this time, the second power supply 226 is constantly being charged by the power supplied by the first power supply 23.

If the charge remaining in the first power supply 23 becomes lower than the charge remaining in the second power supply 226, as a result of the endoscope camera 2 being used (if the electric potential at the connecting position P1 between the power supply line PL and the wireless power supply receiving unit 225 becomes lower than the electric potential at the auxiliary power supply line PLA), the camera head 22 is driven by the power supplied by the second power supply 226. The first power supply 23 then needs to be replaced. In such a case, with the monitoring function described above, the camera circuit 227 recognizes that the remaining charge in the first power supply 23 is dropping below the level suitable for driving the camera head 22, and causes the notifying unit 224 to notify information prompting a medical practitioner or the like to replace the first power supply 23, by controlling the operation of the notifying unit 224. The second power capacity may only need to have a power capacity capable of driving the camera head 22 for the time sufficient for the first power supply 23 to be replaced (5 minutes to 10 minutes or so, for example).

When the remaining charge in the second power supply 226 becomes lower than the second threshold before the replacement of the first power supply 23 is completed, as a result of continuing to use the endoscope camera 2 while the first power supply 23 is being replaced, the camera circuit 227 determines, with the monitoring function described above, that the remaining charge in the second power supply 226 is dropping below the level suitable for driving the camera head 22, and causes the notifying unit 224 to notify information indicating that the driving of the camera head 22 may stop.

If the replacement of the first power supply 23 is completed before the remaining charge in the second power supply 226 becomes lower than the second threshold, the camera head 22 starts being driven and the second power supply 226 starts being charged by the power supplied from the first power supply 23, without the notification of the information described above.

The endoscope camera 2 according to the first embodiment explained above includes the camera head 22, and the first power supply 23, and the second power supply 226. The camera head 22 is then enabled to be driven by receiving the power supply from one of the first power supply 23 and the second power supply 226. Therefore, even when the remaining charge in one of the first power supply 23 and the second power supply 226 becomes low, the endoscope camera 2 is kept operable by receiving power supply from the other one of the first power supply 23 and the second power supply 226.

In particular, the second power supply 226 is charged by the first power supply 23. The first power supply 23 is removable from the camera head 22. Therefore, when the remaining charge in the second power supply 226 is low, the second power supply 226 is charged by, while the camera head 22 is driven by, the power supplied from the first power supply 23. When the remaining charge in the first power supply 23 becomes low, and the first power supply 23 is removed from the camera head 22 so that the first power supply 23 is replaced, and the camera head 22 is driven by the power supplied from the second power supply 226.

Therefore, even when the charge remaining in one of the first power supply 23 and the second power supply 226 becomes low, the endoscope camera 2 is kept operable, and the image disappearance due to the low charge remaining in the power supply may be prevented (the endoscope camera 2 may be prevented from becoming inoperable), advantageously.

The second power supply 226 has a smaller power capacity than the first power supply 23. In other words, the second power supply 226 may be provided with a small power supply (capacitor 2261) having a power capacity only capable of driving the camera head 22 for the time sufficient for the first power supply 23 to be replaced. Therefore, even when two power supplies including the first power supply 23 and the second power supply 226 are mounted on the endoscope camera 2, reductions in the size and the weight of the endoscope camera 2 are not prevented thereby.

The endoscope camera 2 according to the first embodiment communicates wirelessly with the external control device 6 over the predetermined communication protocol (Wi-Fi (registered trademark)).

In other words, because the endoscope camera 2 is cableless, the ease-of-use of the endoscope camera 2 may be improved, and the convenience may be improved.

When the power supply main unit 232 is provided as a secondary battery such as a lithium ion battery, it might be difficult to sterilize the sterilized enclosure 231 in a high-temperature and high-pressure environment, such as that in an autoclave.

In the endoscope camera 2 according to the first embodiment, the first power supply 23 includes the power supply main unit 232 and the sterilized enclosure 231, and the power supply main unit 232 may be attached to and removed from the camera head 22 while the power supply main unit 232 remains covered by the sterilized enclosure 231.

Therefore, by using the sterilized enclosure 231, the power supply main unit 232 may be used without sterilizing the power supply main unit 232.

Furthermore, the endoscope camera 2 according to the first embodiment detects the status of the first power supply 23 and the second power supply 226, and notifies the detection result.

Therefore, when the charge remaining in the first power supply 23 is dropping below the level suitable for driving the camera head 22, the medical practitioner or the like may be prompted to replace the first power supply 23. When the charge remaining in the second power supply 226 is dropping below the level suitable for driving the camera head 22, it is possible to allow the medical practitioner or the like to recognize that the driving of the camera head 22 may stop. Therefore, the medical practitioner or the like may take appropriate actions by receiving the notification of the detection result.

Furthermore, in the endoscope camera 2 according to the first embodiment, the first power supply 23 connects contactlessly and supplies power wirelessly to the camera head 22.

Therefore, it is not necessary to provide the sealed enclosure 221 or the sterilized enclosure 231 with an electrical contact for connecting the first power supply 23 and the camera head 22. In other words, the electric contacts do not need to be water-proofed considering the sterilization in the autoclave or the like, so that the structures of the sealed enclosure 221 and the sterilized enclosure 231 may be simplified.

Modification of First Embodiment

Used in the first embodiment described above is an example in which the endoscope camera 2 includes the rigid inserted portion 21 that uses the relay lens 213 to guide the image of the subject from the tip of the inserted portion 21 to the base end thereof, but the present disclosure is not limited thereto. The endoscope camera may use a flexible inserted portion using an optical fiber, instead of the relay lens 213, for example, or a tip-sensor inserted portion having the tip thereof provided with an image sensor and outputting an image signal picked up by the image sensor wirelessly to the camera circuit 227.

Figure 5:
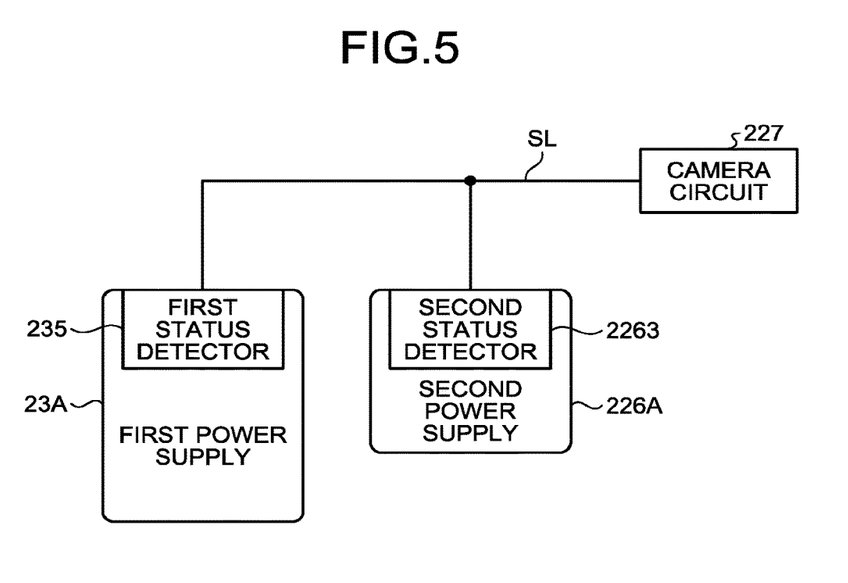
FIG. 5 is a schematic illustrating a modification of the first embodiment, illustrating another example of the function of the camera circuit monitoring the charge remaining in the power supply.

FIG. 5 is a schematic illustrating a modification of the first embodiment, illustrating another example of the function of the camera circuit 227 for monitoring the charge remaining in the power supply.

In the first embodiment described above, the first status detector 228 and the second status detector 229 (FIG. 3) are used as the function of the camera circuit 227 for monitoring the charge remaining in the power supply, but the present disclosure is not limited thereto, and the monitoring function illustrated in FIG. 5 may also be used.

Specifically, a first power supply 23A according to this modification includes, as illustrated in FIG. 5, a first status detector 235, in addition to the members 231 to 233 (not illustrated in FIG. 5).

The first status detector 235 is a part that detects the charge remaining in the power supply main unit 232 in the same manner as the first status detector 228 explained in the first embodiment, and is an integrated circuit (IC) provided internal of the first power supply 23A. The first status detector 235 then outputs the detection result (the charge remaining in the power supply main unit 232) to the camera circuit 227 via the signal line SL (FIG. 5).

In FIG. 5, for the convenience of explanation, the first power supply 23A and the camera circuit 227 are connected over the wire via the signal line SL, and the detection result from the first status detector 235 is output to the camera circuit 227 via the signal line SL, but the present disclosure is not limited thereto, and the detection result may be transmitted wirelessly to the camera circuit 227.

A second power supply 226A according to this modification includes a second status detector 2263, in addition to the members 2261, 2262 (not illustrated in FIG. 5), as illustrated in FIG. 5.

The second status detector 2263 is a part that detects the charge remaining in the capacitor 2261, in the same manner as the second status detector 229 explained in the first embodiment, and is provided as an integrated circuit (IC) provided internal of the second power supply 226. The second status detector 2263 then outputs the detection result (the charge remaining in the capacitor 2261) to the camera circuit 227 via the signal line SL (FIG. 5).

Using such a configuration, the camera circuit 227 receives the detection results from the first status detector 235 and the second status detector 2263, in the same manner as in the first embodiment described above, constantly monitors the status of the first power supply 23A and the second power supply 226A, and controls the operation of the notifying unit 224 depending on the monitoring results.

Figure 6:
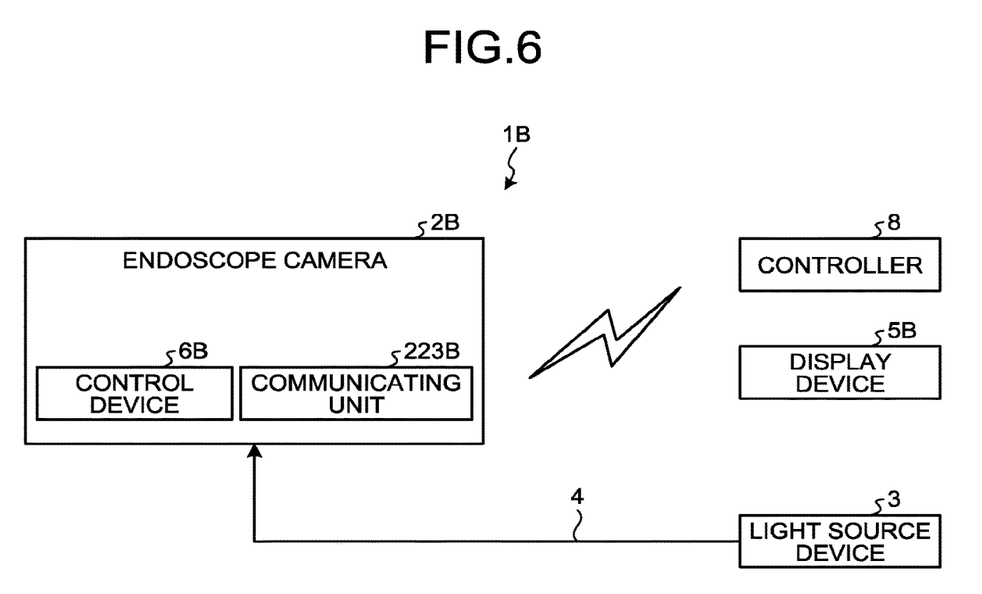
FIG. 6 is a schematic illustrating a modification of the first embodiment, illustrating another example of the endoscope camera system.

FIG. 6 is a schematic illustrating a modification of the first embodiment, illustrating another example of the endoscope camera system 1.

In the first embodiment described above, an endoscope camera 2B (endoscope camera system 1B) added with the function of the control device 6 may be used, as illustrated in FIG. 6, instead of the endoscope camera 2.

In FIG. 6, for the convenience of explanation, the inserted portion 21, the second power supply 226, and the members 221, 222, 224 to 227 of the camera head 22 are not illustrated.

Specifically, in the endoscope camera 2B, a control device 6B having the same function as the control device 6 is added to the camera head 22, for example. A communicating unit 223B according to this modification then connects to communicate with the external device (a display device 5B and a controller 8, in the example illustrated in FIG. 6) over a predetermined communication protocol (for example, Wi-Fi (registered trademark)), and transmits and receives various types of information wirelessly.

The controller 8 is a remote controller for remotely controlling the endoscope camera 2B, and includes a button, a switch, a touch panel, and the like, and receives user operations. The controller 8 then connects to communicate with the endoscope camera 2B over the predetermined communication protocol, and transmits instruction signals that are based on user operations wirelessly to the endoscope camera 2B. The display device 5B connects to communicate with the endoscope camera 2B over the predetermined communication protocol, receives the video signals processed by and wirelessly transmitted by the endoscope camera 2B (control device 6B), and displays the captured image that is based on the video signals.

In the first embodiment and this modification, the camera circuit 227 may monitor the charge remaining in the first power supply 23 and the second power supply 226, and notify (display) the display device 5, 5B or the controller 8 of the monitoring results, in addition to the notifying unit 224.

Furthermore, in the first embodiment and this modification, the communicating unit 223, 223B may be provided externally to the camera head 22, without limitation to a configuration in which the communicating unit 223, 223B is provided internally to the camera head 22.

Figure 7:
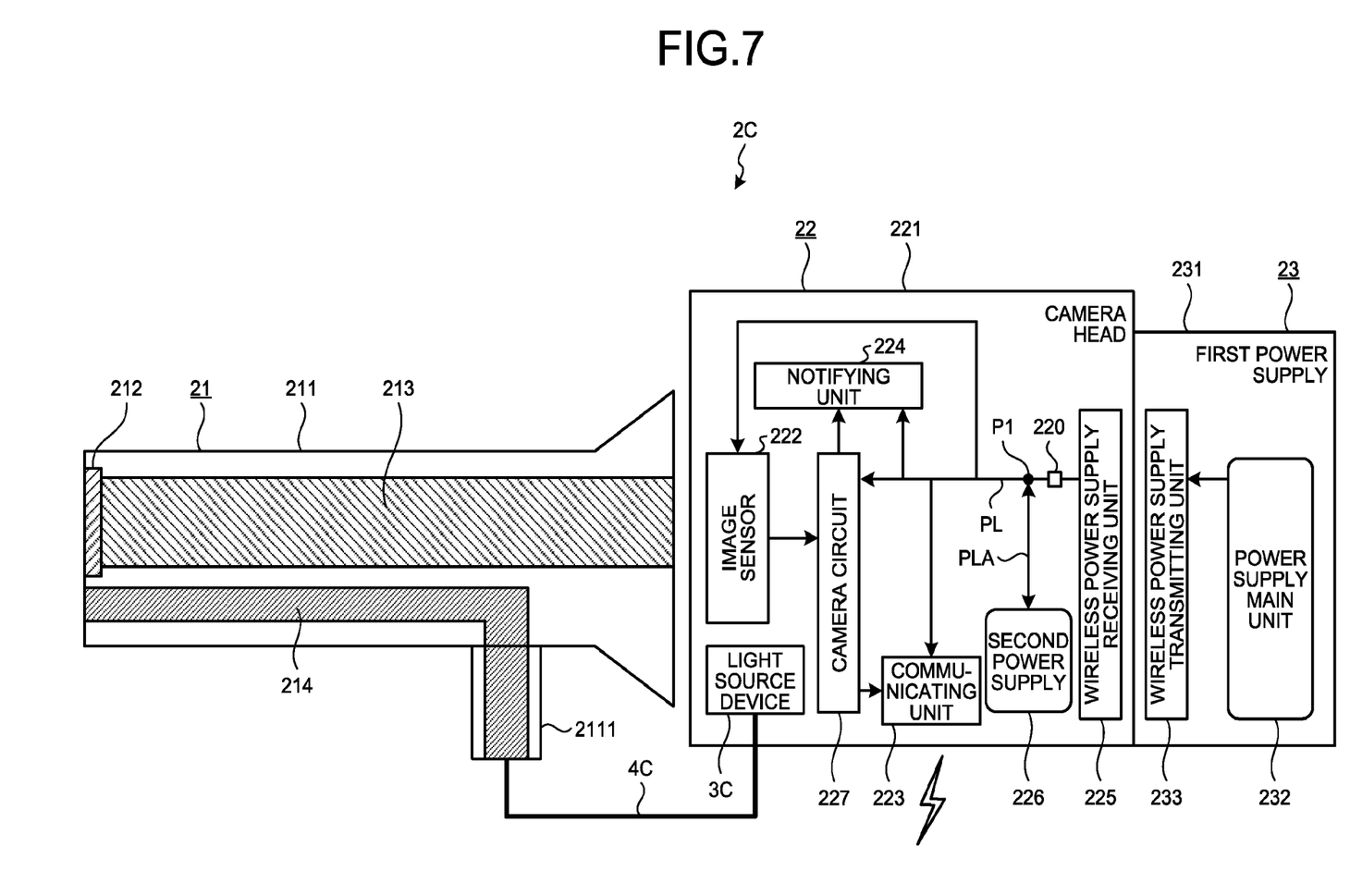
FIG. 7 is a schematic illustrating a modification of the first embodiment, illustrating another example of the endoscope camera.

FIG. 7 is a schematic illustrating a modification of the first embodiment, illustrating another example the endoscope camera 2.

In the first embodiment described above, an endoscope camera 2C in which the camera head 22 includes an internal light source device 3C, as illustrated in FIG. 7, may be used instead of the endoscope camera 2.

The light source device 3C according to this modification is provided as a light emitting diode (LED) light source, for example. The light flux emitted from the light source device 3C is supplied to the insertion tube 211 via a light guide cable 4C.

The light guide cable 4C may also be omitted, and the light source device 3C may be directly connected to the connection connector 2111 of the insertion tube 211 so that the light is directly supplied to the insertion tube 211 from the light source device 3C.

Figure 8:
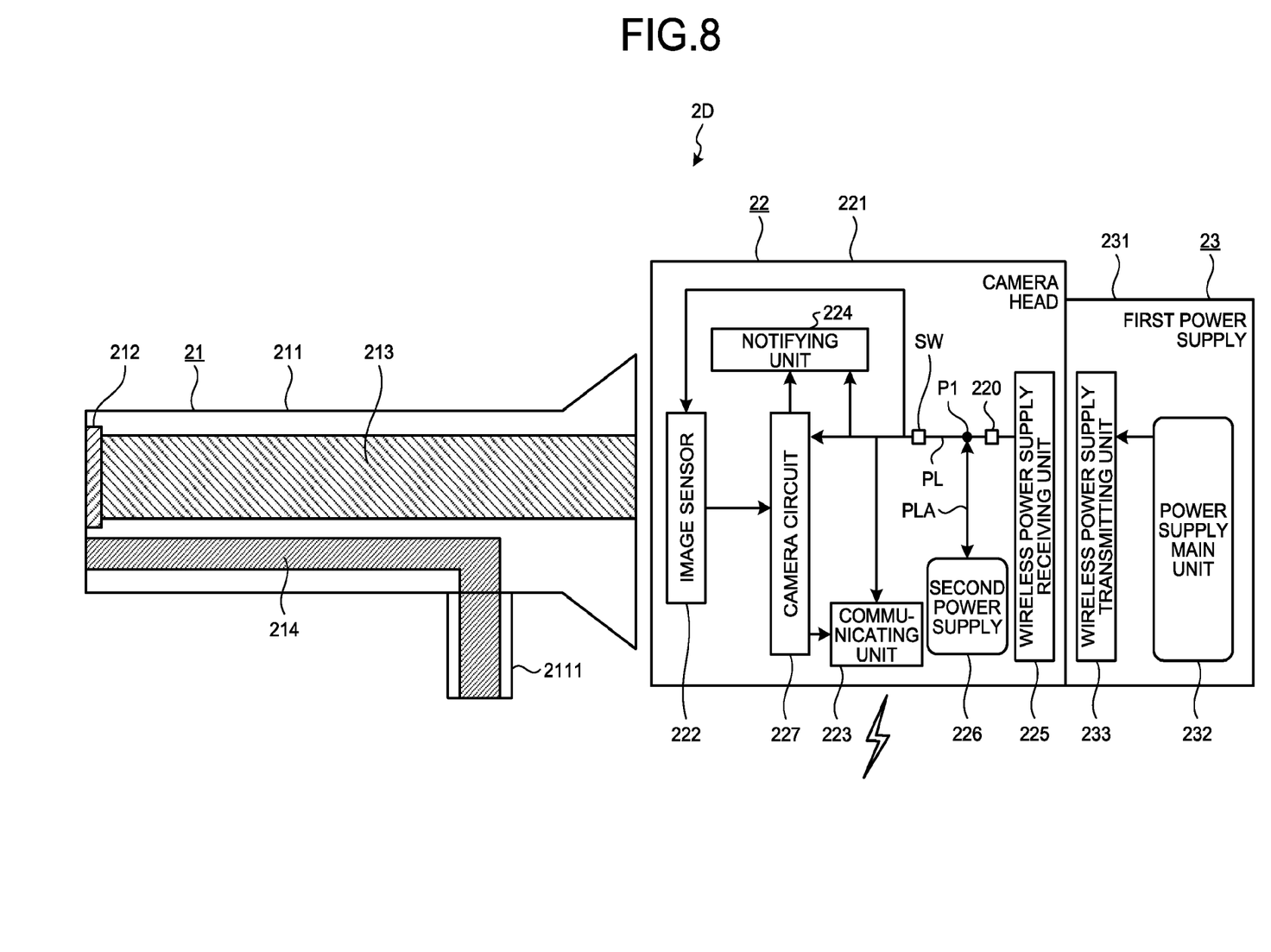
FIG. 8 is a schematic illustrating a modification of the first embodiment, illustrating another example of the endoscope camera.

FIG. 8 is a schematic illustrating a modification of the first embodiment, illustrating another example of the endoscope camera 2.

In the first embodiment described above, an endoscope camera 2D having the camera head 22 including a status switching unit SW, as illustrated in FIG. 8, may be used instead of the endoscope camera 2.

The status switching unit SW is provided as a mechanical switch that is operated by the medical practitioner or the like, and is provided subsequently to the connecting position P1 at which the power supply line PL is connected to the auxiliary power supply line PLA (provided on the side away from the wireless power supply receiving unit 225). When the status switching unit SW is switched ON by the medical practitioner or the like, the status switching unit SW is switched to a permitted state permitting power feeding from the first power supply 23 or the second power supply 226 to the image sensor 222, the communicating unit 223, the notifying unit 224, and the camera circuit 227. When the status switching unit SW is switched OFF by the medical practitioner or the like, by contrast, the status switching unit SW is switched to a prohibited state prohibiting such power feeding. In other words, the status switching unit SW has a function as a power supply switch.

With such a configuration, by keeping the status switching unit SW OFF while the endoscope camera 2 is not in use, discharging of the first power supply 23 and the second power supply 226 may be prevented, and the reduction of the usable time of the endoscope camera 2 may be prevented.

Without limitation to the configuration in which the power supply switch is provided as a mechanical switch (status switching unit SW), the power supply switch may also be provided as what is called an electronic switch using a field effect transistor (FET), a transistor, or a switch IC, for example.

Specifically, a power supply control IC is provided to the camera circuit 227. Electronic switches are then respectively provided between the power supply line PL and the elements of the camera circuit 227 other than the power supply control IC, between the power supply line PL and the image sensor 222, and between the power supply line PL and the notifying unit 224. In other words, electronic switches are not provided between the power supply line PL and the power supply control IC, and between the power supply line PL and the communicating unit 223, so that the power is constantly supplied to the power supply control IC and the communicating unit 223 by the first power supply 23 or the second power supply 226.

When the control device 6 is powered ON, and the communicating unit 223 receives the power ON signal from the control device 6, the power supply control IC turns on the electronic switches to be in the permitted state in which the first power supply 23 or the second power supply 226 is permitted to supply power to the elements of the camera circuit 227 other than the power supply control IC, to the image sensor 222, and to the notifying unit 224. When the control device 6 is powered OFF, and the communicating unit 223 receives the power OFF signal from the control device 6, the power supply control IC turns off the electronic switches to be in the prohibited state in which power supply is prohibited.

When the elements of the camera circuit 227 other than the power supply control IC, the image sensor 222, and the notifying unit 224 are provided with what is called power supply ICs for generating a sufficient voltage for itself, and when the power supply may be turned on and off by such power supply ICs, those power supply ICs are included as an example of the electronic switch described above.

Second Embodiment

A second embodiment of the present disclosure will now be explained.

In the explanation hereunder, the elements that are the same as those according to the first embodiment described above are assigned with the same reference numerals, and the explanations thereof will be omitted or simplified.

In the first embodiment described above, the endoscope camera 2 is used as an example of the medical tool according to the present disclosure.

By contrast, the second embodiment is different from the first embodiment described above in that an energy treatment tool is used as an example of the medical tool according to the present disclosure.

Figure 9:
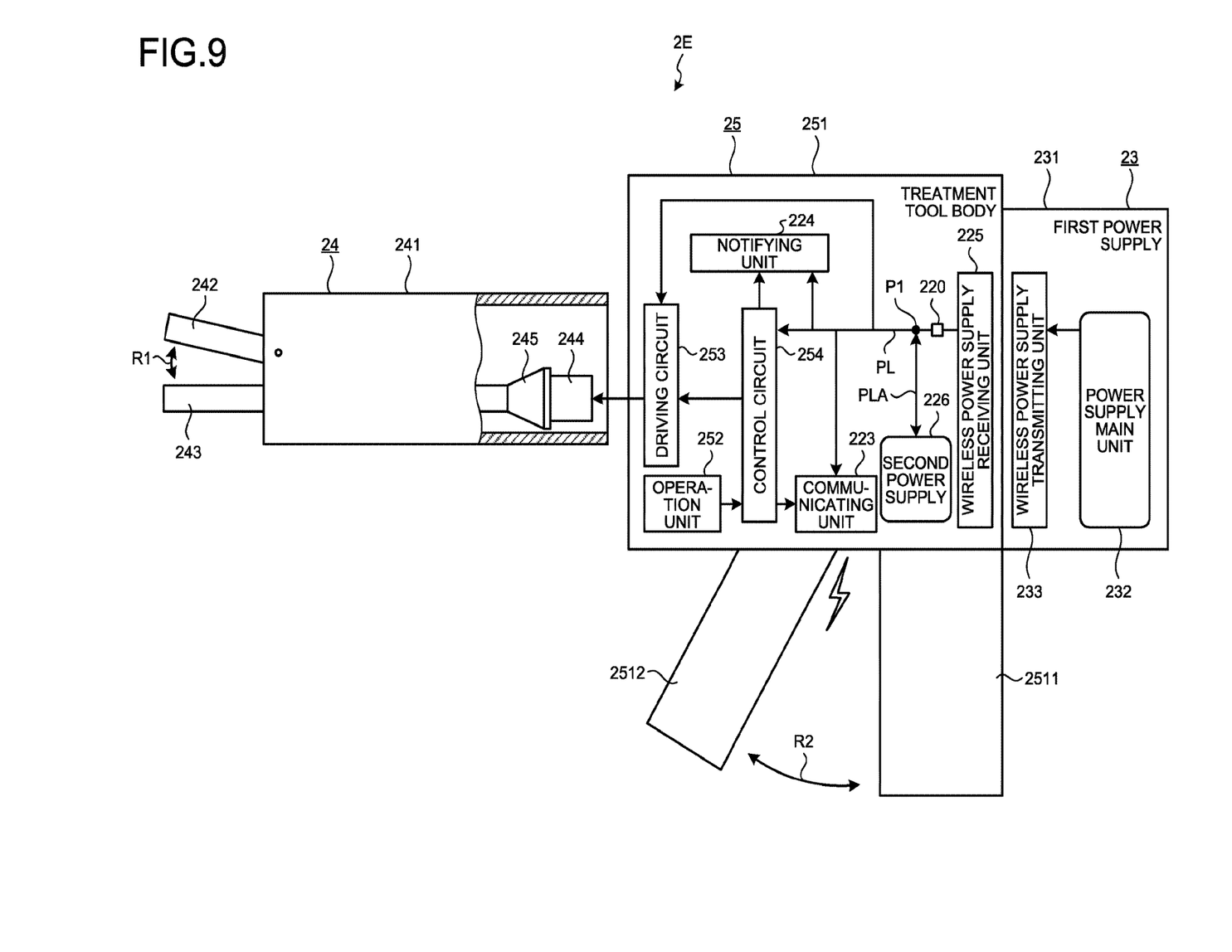
FIG. 9 is a schematic illustrating a configuration of an energy treatment tool according to a second embodiment of the present disclosure.

FIG. 9 is a schematic illustrating an energy treatment tool 2E according to the second embodiment.

Specifically, the energy treatment tool 2E treats a target region by applying energy (ultrasonic energy in the second embodiment) to the biological tissues to be treated (e.g., to be joined (or inosculated) or to be dissected) (hereinafter, referred to as a target region). In the second embodiment, the energy treatment tool 2E is a linear-type surgical treatment tool for treating the target region through the abdominal wall. This energy treatment tool 2E includes, as illustrated in FIG. 9, a treating unit 24 and a treatment tool body 25, in addition to the first power supply 23 explained in the first embodiment.

The treating unit 24 is a part that holds the target region between their tips, and treats the target region. The treating unit 24 includes, as illustrated in FIG. 9, a shaft 241 and an organization gripping portion 242.

A probe 243 includes an ultrasonic transducer 244 and a vibration enhancing member 245.

The shaft 241 has a substantially cylindrical shape, and one end of the shaft 241 is connected to a sealed enclosure 251 providing a cladding to the treatment tool body 25. The organization gripping portion 242 is movably supported in the direction of the arrow R1 (FIG. 9) about an axis on the other end of the shaft 241.

Attached to the sealed enclosure 251 are a handle 2511 to be held by the medical practitioner or the like, and an operation knob 2512 supported about an axis in a movable manner in the directions of the arrow R2 with respect to the sealed enclosure 251, as illustrated in FIG. 9.

Installed internal of the shaft 241 are an opening and closing mechanism (not illustrated) that enables the organization gripping portion 242 to be opened and to be closed in the directions of the arrow R1 (FIG. 9), in response to an operation of the operation knob 2512 performed by the medical practitioner or the like, the probe 243, the ultrasonic transducer 244, and the vibration enhancing member 245.

The organization gripping portion 242 is a part that opens and closes in the directions of the arrow R1 in response to an operation of the operation knob 2512 performed by the medical practitioner or the like, and holds the target region with the probe 243.

The probe 243 has a pillar like shape extending in the axial direction of the shaft 241. This probe 243 is inserted into one end of the shaft 241, while the one end of the probe 243 (the left end side in FIG. 9) is exposed to the external, as illustrated in FIG. 9, and the ultrasonic transducer 244 and the vibration enhancing member 245 are installed in the other end of the probe 243. The probe 243 is then brought into contact with the target region, gripping the target region with the organization gripping portion 242, and communicates the ultrasonic vibrations generated by the ultrasonic transducer 244 to the target region (applies the ultrasonic energy to the target region).

The ultrasonic transducer 244 is provided as a piezoelectric transducer using piezoelectric elements that shrink and extend in response to application of the AC voltage, for example. The ultrasonic transducer 244 generates ultrasonic vibrations in response to the AC voltage applied thereto under the control of the treatment tool body 25.

The vibration enhancing member 245 is interposed between the other end of the probe 243 and the ultrasonic transducer 244, and is provided as a horn or the like communicating the ultrasonic vibrations generated by the ultrasonic transducer 244 to the probe 243.

As the ultrasonic transducer 244 and the vibration enhancing member 245, the probe 243 may be configured to vibrate in the longitudinal directions (to vibrate in the axial direction of the probe 243), or the probe 243 may be configured to vibrate in the lateral directions (to vibrate in the radial directions of the probe 243).

The treatment tool body 25 has the function of the tool main unit according to the present disclosure. The treatment tool body 25 includes, as illustrated in FIG. 9, the sealed enclosure 251, an operation unit 252, a driving circuit 253, and a control circuit 254, in addition to the communicating unit 223, the notifying unit 224, the wireless power supply receiving unit 225, and the second power supply 226 explained in the first embodiment.

The sealed enclosure 251 is different from the sealed enclosure 221 explained in the first embodiment in that the sealed enclosure 251 is provided with the handle 2511 and the operation knob 2512. In other words, a connecting unit (not illustrated) to be mechanically connected (connected electrically contactlessly) with the first power supply 23 is provided to the external surface of the sealed enclosure 251, in the same manner as in the sealed enclosure 221. The members 223 to 226, 253, and 254 are housed inside of the sealed enclosure 221.

The operation unit 252 is provided in a manner exposed to the external surface of the sealed enclosure 251, as a button or a switch to be operated by the medical practitioner.

The driving circuit 253 is driven by receiving the power supply by the first power supply 23 or the second power supply 226 via the power supply line PL, and applies the AC voltage to the ultrasonic transducer 244 under the control of the control circuit 254.

The control circuit 254 includes a CPU or the like, is driven by receiving the power supply from the first power supply 23 or the second power supply 226 via the power supply line PL, and controls the entire treatment tool body 25. Specifically, the control circuit 254 has a monitoring function for monitoring the charge remaining in the first power supply 23 and the second power supply 226 (see FIGS. 3 and 5), causes the notifying unit 224 to notify the monitoring results, in the same manner as the camera circuit 227 explained in the first embodiment. The control circuit 254 establishes a communication connection with an external device (such as a display device (not illustrated)) via the communicating unit 223 over a communication protocol such as Wi-Fi (registered trademark), in the same manner as in the camera circuit 227 explained in the first embodiment, and communicates wirelessly with the external device (notifies the external device of the results of monitoring the charge remaining in the first power supply 23 and the second power supply 226 (e.g., displays the results on the display device), for example). The control circuit 254 controls the operation of the driving circuit 253 in response to the operation of the operation unit 252 performed by the medical practitioner or the like (to start causing the driving circuit 253 to apply the AC voltage to the ultrasonic transducer 244).

The way in which the first power supply 23 and the second power supply 226 are charged before the use of the energy treatment tool 2E is the same as the way of charging explained in the first embodiment (see FIG. 4).

The way in which the power is supplied from the first power supply 23 or the second power supply 226 to the treatment tool body 25 is the same as the way in which the power is supplied from the first power supply 23 or the second power supply 226 to the camera head 22, as explained in the first embodiment.

Even when the medical tool according to the present disclosure is the energy treatment tool 2E, as explained in the second embodiment described above, the same advantageous effects as those achieved by the first embodiment described above may be achieved.

Modifications of Second Embodiment

The energy treatment tool 2E according to the second embodiment is configured to convert the power supplied from the first power supply 23 or the second power supply 226 into ultrasonic energy, and to treat the biological tissues with the ultrasonic energy, but the present disclosure is not limited thereto. For example, the energy treatment tool according to the present disclosure may be configured to convert the power supplied from the first power supply 23 or the second power supply 226 into energy such as heat, a microwave, or a radio wave, and to treat the biological tissues with the energy. Furthermore, the energy treatment tool according to the present disclosure may be configured to use two or more types of energy out of ultrasonic energy, heat, a microwave, and a radio wave, for example, and to treat the biological tissues with the energy.

The communicating unit 223 is provided internal of the treatment tool body 25 in the second embodiment described above, but the configuration is not limited thereto, and may be provided externally to the treatment tool body 25.

In the second embodiment described above, the status switching unit SW, the power supply control IC, the electronic switch, or the like may also be provided to the treatment tool body 25, in the same manner as the modification of the first embodiment described above (FIG. 8)

Other Embodiments

Explained above are some embodiments according to the present disclosure, but the present disclosure is not limited to the first and the second embodiments, and the modifications thereof.

The endoscope camera 2 (2C) and the control device 6 according to the first embodiment and the modifications thereof connect to communicate with each other over a communication protocol such as Wi-Fi (registered trademark), and transmit and receive image signals, control signals, and the like wirelessly, but the present disclosure is not limited thereto, and may be connected to each other over a wire such as a transfer cable, and may input and output the image signals, the control signals, and the like over the transfer cable or the like.

In the same manner, the energy treatment tool 2E and the external device (not illustrated) according to the second embodiment and the modification thereof may also communicate over a wire such as a transfer cable, without limitation to the configuration in which the communication is performed wirelessly.

Explained in the first embodiment and the modifications thereof, for the convenience of explanation, is an example in which the inserted portion 21, the camera head 22, and the first power supply 23 (23A) are all included in the medical tool according to the present disclosure (endoscope camera), but the medical tool according to the present disclosure (endoscope camera) may merely need to include the camera head 22, the first power supply 23 (23A), and the second power supply 226 (226A), and a configuration including the camera head 22 and the first power supply 23 (23A), excluding the inserted portion 21, also corresponds to the medical tool according to the present disclosure (endoscope camera).

In the same manner, in the second embodiment and the modification thereof described above, a configuration including only the treatment tool body 25 and the first power supply 23, but not the treating unit 24, also corresponds to the medical tool according to the present disclosure (energy treatment tool).

In the first embodiment and the modifications thereof, the second power supply 226 (226A) are provided internal of the sealed enclosure 221, but the present disclosure is not limited thereto, and the second power supply 226 (226A) may be provided as a separate unit from the camera head 22, in the same manner as the first power supply 23 (23A), and may be removable from the camera head 22.

In the second embodiment and the modification thereof described above, the second power supply 226 may also be provided as a separate unit from the treatment tool body 25, and may be removable from the treatment tool body 25.

Furthermore, while the capacitor 2261 is included in the second power supply 226 (226A) according to the first and the second embodiments and the modifications thereof described above, a secondary battery may be used instead of the capacitor 2261.

The first power supply 23 (23A) and the second power supply 226 (226A) according to the first and the second embodiments and the modifications thereof described above are charged by the wireless power supply from the external power supply 7, but the present disclosure is not limited thereto. The first power supply 23 (23A), the second power supply 226 (226A), and the external power supply 7 may be connected over the wire using a power supply cable or a universal serial bus (USB) cable, and the first power supply 23 (23A) and the second power supply 226 (226A) may be charged by allowing the first power supply 23 (23A) and the second power supply 226 (226A) to receive power supply from the external power supply 7 via the cable.

Furthermore, the external power supply 7 is used to charge the first power supply 23 (23A) and the second power supply 226 (226A) before the use of the endoscope camera 2 or the energy treatment tool 2E, but the present disclosure is not limited thereto. The power may also be supplied to the camera head 22 (second power supply 226 (226A)) or the treatment tool body 25 (second power supply 226), and the first power supply 23 (23A) wirelessly or over the wire during the use of the endoscope camera 2 (energy treatment tool 2E), and the first power supply 23 (23A) and the second power supply 226 (226A) may be charged while the camera head 22 or the treatment tool body 25 is driven by the external power supply 7. With such a configuration, during the ordinary use of the endoscope camera 2 (2B, 2C) or the energy treatment tool 2E, the camera head 22 or the treatment tool body 25 may be driven by the power supplied from the external power supply 7, and, when the power supplied from the external power supply 7 stops due to a power failure, for example, the camera head 22 or the treatment tool body 25 may be driven by the power supplied from the first power supply 23 (23A). When the charge remaining in the first power supply 23 (23A) becomes low, the camera head 22 or the treatment tool body 25 may be driven by the power supplied from the second power supply 226 (226A), as explained in the first embodiment.

Explained in the first and the second embodiments and the modifications thereof described above is an example in which the first power supply 23 (23A) and the second power supply 226 (226A) are connected to the same power supply line PL, and the power is automatically supplied by one of the first power supply 23 (23A) and the second power supply 226 (226A) whichever the electric potential is higher, but the present disclosure is not limited thereto. For example, a selecting unit may be used to select one of the first power supply 23 (23A) and the second power supply 226 (226A) based on the remaining charge in the first power supply 23 (23A) and the second power supply 226 (226A).

The medical tool according to the present disclosure includes a tool main unit, a first power supply and a second power supply. The tool main unit is enabled to be driven by receiving the supply of power from one of the first power supply and the second power supply. Therefore, even when the power remaining in one of the first power supply and the second power supply becomes low, the medical tool is made operable by receiving the supply of power from the other one of the first power supply and the second power supply.

In particular, the second power supply is charged by the first power supply. In addition, the first power supply is removable from the tool main unit. Therefore, when the charge remaining in the second power supply is low, the tool main unit is driven by and the second power supply is charged by the power supplied from the first power supply. When the charge remaining in the first power supply becomes low, and when the first power supply is removed to be replaced from the tool main unit, the tool main unit is driven by the power supplied from the second power supply.

Therefore, even when the power remaining in one of the first power supply and the second power supply becomes low, the medical tool remains operable, and may be prevented from becoming inoperable due to the low remaining charge in the power supply, advantageously.

The second power supply has a smaller power capacity that the first power supply does. In other words, the second power supply may be provided as a small power supply having such a power capacity that enables the tool main unit to be driven for only a time period for replacing the first power supply. Therefore, mounting two power supplies including the first power supply and the second power supply on the medical tool does not prevent reductions in size and weight of the medical tool.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical tool comprising:
a main tool to be driven in response to a power supply;
a first power supply that is removable from the main tool;
a second power supply in the main tool, the second power supply having a smaller power capacity than the first power supply, and being wirelessly charged by the first power supply,
a first status detector to detect a remaining charge of the first power supply;
a second status detector to detect a remaining charge of the second power supply; and
a circuit within the main tool to monitor remaining charges of the first power supply and the second power supply, wherein
the main tool is to be driven by receiving power from one of the first power supply and the second power supply, and
under a condition that the circuit determines that the remaining charge in the first power supply is less than the remaining charge in the second power supply, the main tool is to be driven by the second power supply.

2. The medical tool according to claim 1, wherein the second power supply has a smaller power capacity than the first power supply, the second power supply being charged by the first power supply, and including a capacitor for power feeding.

3. The medical tool according to claim 1, further comprising a communicator to wirelessly communicate with an external device.

4. The medical tool according to claim 1, wherein
the first power supply includes:
a main power supply to supply power; and
a sterilized enclosure, wherein
the first power supply is removable from the main tool with the main power supply being covered by the sterilized enclosure.

5. The medical tool according to claim 1, wherein the main tool includes the second power supply.

6. The medical tool according to claim 1, further comprising:
an output to notify a user of the condition.

7. The medical tool according to claim 1, wherein the first power supply contactlessly connects to the main tool.

8. The medical tool according to claim 1, further comprising a status switch to switch between a permitted state and a restricted state, the permitted state permitting power feeding from the first power supply or the second power supply to the main tool, and the restricted state restricting the power feeding.

9. The medical tool according to claim 1, wherein the medical tool is an endoscope camera configured to image an interior of a subject.

10. The medical tool according to claim 1, wherein the medical tool is an energy treatment tool configured to treat a biological tissue by applying energy to the biological tissue.

\* \* \* \* \*